United States Patent [19]
Fertel et al.

[11] Patent Number: 4,994,606
[45] Date of Patent: Feb. 19, 1991

[54] PROCESS FOR THE PREPARATION OF 4,5-DIFLUOROANTHRANILIC ACID FROM 4,5-DIFLUOROPHTHALIC ANHYDRIDE OR 4,5-DIFLUOROPHTHALIC ACID

[75] Inventors: Lawrence B. Fertel, Buffalo; Henry C. Lin, Grand Island, both of N.Y.

[73] Assignee: Occidental Chemical Corporation, Niagara Falls, N.Y.

[21] Appl. No.: 532,764

[22] Filed: Jun. 4, 1990

Related U.S. Application Data

[63] Continuation-in-part of Ser. No. 439,228, Nov. 20, 1989, Pat. No. 4,937,377.

[51] Int. Cl.$^5$ ............................................ C07C 229/00
[52] U.S. Cl. .................................... 562/456; 562/479; 562/458
[58] Field of Search ...................... 562/456, 479, 458

[56] References Cited

FOREIGN PATENT DOCUMENTS 701795 1/1965 Canada .
3409244 9/1985 Fed. Rep. of Germany .

OTHER PUBLICATIONS

Graw, J. D. et al, J. Chem. Eng. Data 13(4), 587–588, 1968.

Primary Examiner—Paul J. Killos
Attorney, Agent, or Firm—James F. Tao; John H. Engelmann

[57] ABSTRACT

4,5-Difluoroanthranilic acid may be prepared by decarboxylating 4,5-difluorophthalic anhydride or 4,5-difluorophthalic acid by heating in dimethyl acetamide, N-methyl-2-pyrrolidone or quinoline, optionally by reaction with copper, copper oxide, copper salts, or halides and salts of Zn, Cd, Ag and Ni as a catalyst, whereby 3,4-difluorobenzoic acid is formed; nitrating said 3,4-difluorobenzoic acid in a mixture of nitric and sulfuric acids to form 2-nitro-4,5-difluorobenzoic acid, and reducing said 2-nitro-4,5-difluorobenzoic acid to form 4,5-difluoroanthranilic acid.

27 Claims, No Drawings

PROCESS FOR THE PREPARATION OF 4,5-DIFLUOROANTHRANILIC ACID FROM 4,5-DIFLUOROPHTHALIC ANHYDRIDE OR 4,5-DIFLUOROPHTHALIC ACID

BACKGROUND OF THE INVENTION

This application is a continuation-in-part of U.S. Ser. No. 07/439,228, filed 11/20/89, now U.S. Pat. No. 4,937,377 copending herewith.

This invention relates to a method for the preparation of 4,5-difluoroanthranilic acid from 4,5-difluorophthalic anhydride or 4,5-difluorophthalic acid. 4,5-Difluoroanthranilic acid is a known and useful chemical intermediate. For example, it has been used as an intermediate in the preparation of quinolone antibiotics. It can also be converted further to other useful fluorinated intermediates, such as 3,4-difluoro aniline.

4,5-Difluoroanthranilic acid has previously been prepared from 4,5-difluourophthalic anhydride by reaction with ammonia followed by a Hoffmann rearrangement using aqueous sodium hypochlorite (U.S. Pat. No. 4,343,951). It has also been prepared by treating 5,6-difluoro-1H-indolo-2,3-dione with basic hydrogen peroxide (U.S. Pat. No. 4,833,270). The hydrochloride salt has been prepared from 3,4-difluorobenzoic acid by nitration to form 4,5-difluoro-2-nitrobenzoic acid, and subsequent reduction with hydrogen in the presence of a rhodium on carbon catalyst. (Joseph D. Graw, Michael Corey and W. A. Skinner, J. Chem. Eng. Data, 13 (4) 587 (1968)).

4-Fluoroanthranilic acid has been prepared by the iron/HCl reduction of 4-fluoro-2-nitrobenzoic acid (J. Jillek, Czech. Patent CS246349 B1 as abstracted in Chem. Abstracts 110:75056(w)).

The intermediate 3,4-difluorobenzoic acid has been prepared by the oxidation of the corresponding toluene derivative (G. Valkanas, J. Org. Chem., 27 (1962) 2923).

Many examples of decarboxylation reactions have been reported. Basic substances have been used to catalyze such reactions. For example, it is disclosed in D. S. Tarbell, et al Org. Syn., Coll. Vol. III (1955) 267, that 3,5-dichloro-4-hydroxybenzoic acid may be decarboxylated by vigorous heating in N,N-dimethylaniline. It is disclosed in A. Singer and S. M. McElvane, Org. Syn., Coll. Vol. II (1943) 214, that 3,5-dicarboxy-2,6-dimethylpyridine di-potassium salt may be completely decarboxylated by heating the salt in the presence of calcium hydroxide. Copper and copper salts have been used to catalyze decarboxylation reactions. For example, H. R. Snyder et al, Org. Syn., Coll. Vol. III (1955) 471 disclose the use of a copper oxide catalyst for the decarboxylation of imidazole 4,5-dicarboxylic acid.

Some compounds may be decarboxylated without catalysts. For example, C. Wang, Bul. Inst. Kim. Acad. Sinica, No. 2156 (1972), as abstracted in Chem. Abstracts (CA79 (15):91729), discloses that tetrachloro or tetrabromophthalic acids, or their anhydrides, may be decarboxylated to the corresponding benzoic acids when refluxed in dimethyl formamide. 3-nitrophthalic acid underwent a similar reaction.

Decarboxylation is not always a predictable reaction. For example, A. S. Sultanov, J. Gen. Chem. (USSR) 16 1835 (1946) as abstracted in CA 41:6223(e) discloses that salicylic acid may be decarboxylated by autoclaving the acid in the presence of copper bronze and benzene at 170° C. The acid alone decarboxylates at 205° C., while in the presence of aniline decarboxylation begins at 170° C. In the case of salicylic acid, aniline and copper bronze seem to be equal in catalytic ability. On the other hand, when phthalic acid is heated in aniline at 180° C., decarboxylation does not occur and instead phthalic anhydride is produced. Heating phthalic anhydride with copper bronze in chloroform at 180° C. gave a 22% yield of benzoic acid. Phthalic acid was found to decarboxylate to yield benzoic acid merely by heating in water at 235° C.

Decarboxylations of certain fluorophthalic acids have been reported. 3,4,5,6-Tetrafluorophthalic acid decarboxylates under certain conditions to yield 2,3,4,5-tetrafluorobenzoic acid. For example, Japanese Patent JP 61/85349 A2[86/85349] as abstracted in Chem. Abstracts (CA105:152719r), discloses that the reaction may be conducted in an aqueous medium at 150 to 230° C. The reaction may be carried out at a lower temperature (100 to 250° C.) in the presence of copper, zinc, cadmium, iron, cobalt, nickel, other oxides, hydroxides and/or carbonates. Japanese Patent Application 86/103,317 as abstracted in Chem. Abstracts (CA105 (22):193368u), discloses that the above reaction may be conducted in an aqueous medium at a pH of 0.7-2.2 at a temperature of 100°-200° C. The pH of the medium is adjusted by acidifying with sulfuric acid and partial neutralization with calcium hydroxide. Japanese Patent 63/295529m A2[88/295529] as abstracted in Chem. Abstracts (CA 111 (3): 23221X), discloses that the reaction may be conducted at 130° C. in tri-butylamine.

Yacobsen, O. J. discloses in Zh. Obsch. Khim. 36 (1966) page 139 (as appearing in Journal of General Chemistry of the U.S.S.R. translated from Russian 36 (1966) page 144), that 2,3,4,5-tetrafluorophthalic acid may be decarboxylated to yield 2,3,4,5-tetrafluorobenzoic acid by heating for one hour at 145° C. in dimethyl formamide solvent.

Japanese Patent JP 01/52737 as abstracted in Chem. Abstract (CA)111 (14):117305e discloses the preparation of 2,4,5-trifluorobenzoic acid by the decarboxylation of 3,4,6-trifluorophthalic acid in a liquid medium at a temperature of 80°-250° C.

Under slightly more vigorous conditions, Japanese Patent Application 61/43130 A2[86/43130] as abstracted in Chem. Abstracts (CA106 (1):46295), discloses that 3,4,5,6-tetrafluorophthalic acid may be completely decarboxylated to 1,2,3,4-tetrafluorobenzene. The conditions for complete decarboxylation are in an aqueous medium from 210 to 300° C. with the optional presence of a catalyst.

Japanese Patent Application 86/290399 as abstracted in Chem. Abstracts (CA109 (19) 170038e), discloses that 3,5,6-trifluoro-4-hydroxyphthalic acid may be decarboxylated by heating the compound for three hours, in water, under nitrogen atmosphere, at 140° C. (in a sealed tube) to yield 2,4,5-trifluoro-3-hydroxybenzoic acid.

SUMMARY OF THE INVENTION

According to the present invention, 4,5-difluoroanthranilic acid may be prepared from either 4,5 difluorophthalic anhydride or 4,5-difluorophthalic acid. The process of this invention comprises the decarboxylation of either 4,5-difluorophthalic anhydride and 4,5-difluorophthalic acid in N-methyl-2-pyrrolidone, quinoline, or dimethyl acetamide solution optionally using copper, copper oxide, copper salts, or halides and salts of Zn, Cd, Ag and Ni as a catalyst, to yield 3,4- difluorobenzoic acid; the nitration of the 3,4-difluorobenzoic acid in a mixture of nitric and sulfuric acids to form 2-nitro-4,5-difluorobenzoic acid; and the reduction of the 2-nitro-4,5-difluorobenzoic acid to form 4,5-difluoroanthranilic acid.

DETAILED DESCRIPTION OF THE INVENTION

The present invention provides a process for preparing 4,5-difluoroanthranilic acid from 4,5-difluorophthalic anhydride or 4,5-difluorophthalic acid. ; The process involves the decarboxylation of 4,5-difluorophalic anhydride or 4,5-difluorophthalic acid to form 3,4-difluorobenzoic acid, nitration of the 3,4-difluorobenzoic acid to form 2-nitro-4,5-difluorobenzoic acid, and reduction of the nitro compound. The decarboxylation of 4,5,-difluorophthalic anhydride or 4,5-difluorophthalic acid is conducted in N-methylpyrrolidone, quinoline, or dimethyl acetamide. Optionally, copper and salts of Zn, Cd, Ag and Ni may be used as catalysts in the decarboxylation step.

4,5-Difluorophthalic anhydride may be readily prepared by the reaction of 4,5-dichlorophthalic anhydride with potassium fluoride as disclosed in U.S. Pat. No. 4,374,266 (Example I). The acid may be readily prepared by reacting the anhydride with water.

The decarboxylation of 4,5-difluorophthalic anhydride proved to be difficult, since previously known methods of decarboxylation led to a low yield of the desired product along with numerous by-products. The following chart illustrates the decarboxylation methods which were tested. The percentage product shown in the results were those obtained by gas chromatographic analysis, DFBA stands for 3,4-difluorobenzoic acid. s.m. stands for starting material.

| Decarboxylation of 4,5-difluorophthalic anhydride | | |
|---|---|---|
| | Conditions | Results |
| (1) | 150–190°/95% $H_2SO_4$ | No Reaction |
| (2) | 150 N-methyl-2-pyrrolidone No catalyst | No Reaction |
| (3) | 140°/DMF/12 hours No catalyst | 0% DFBA/50% s.m.; 50% other |
| (4) | 150° DMAc/$Cu_2O$/22 hours | 19% DFBA/31% s.m./31% other |
| (5) | 150° DMAc/CuO/27 hours | 27% DFBA/9% s.m./44% other |
| (6) | 150° DMAc/CuO/22 hours | 40% DFBA/12% s.m./36% other |
| (7) | 200° Quinoline/Cu/3 hours | 42% DFBA/51% s.m./7% other |
| (8) | 190° N-methyl-2-pyrrolidone/7 hours | 4% DFBA/74% s.m./22% other |
| (9) | 190° DMSO/10% $Cu_2O$/5 hours | many products |
| (10) | 190° DMSO/10% CuO/5 hours | many products |

Similarly, the decarboxylation of 4,5-difluorophthalic acid proved to be difficult as well. The decarboxylation was attempted using several methods. The results are shown in the chart below:

| Reactions with 4,5-difluorophthalic Acid | | |
|---|---|---|
| | Conditions | Results |
| (1) | 100° 10% $H_2SO_4$/18 hours | No Reaction |
| (2) | 200° 85% $H_2SO_4$ | No Reaction |
| (3) | 170° DMSO/18 hours | No Reaction |
| (4) | 150° Sulfolane | No Reaction |
| (5) | 150° DMSO/LiCl/12 hours | No Reaction |
| (6) | 150° DMSO/NaCl/12 hours | No Reaction |
| (7) | 125° DMAc/No Catalyst | No Reaction |
| (8) | 150° DMAc/22 hours | 0% DFBA, 9% s.m., 91% other |
| (9) | 150° DMAc/CuO | 47% DFBA, 2% s.m. 51% other |
| (10) | 150° DMAc/$Cu_2O$/22 hours | 69% DFBA, 0% s.m., 31% other |
| (11) | 125° DMAc/CuO/22 hours | 60% DFBA, 3% s.m., 37% other |
| (12) | 125° DMAc/$Cu_2O$/22 hours | 70% DFBA, 8% s.m., 22% other |

Surprisingly, we have found that 4,5-difluorophthalic anhydride and 4,5-difluorophthalic acid may be selectively decarboxylated in N-methyl-pyrrolidone, dimethyl acetamide or quinoline to yield 3,4-difluorobenzoic acid.

The selective decarboxylation of 4,5-difluorophthalic acid or 4,5-difluorophthalic anhydride to yield 3,4-difluorobenzoic acid, may be conducted without a catalyst. However, if no catalyst is used, decarboxylation is conducted in a temperature range of 175°–215° C. In addition, without a catalyst, reactions are rather slow. The decarboxylation is preferably conducted using a copper catalyst such as Cu, $Cu_2O$, CuO, $CuSO_4$, $CuCl_2$, CuCl, $CuF_2$, $Cu_2CO_3$, and $Cu(OH)_2$. In addition, halides and salts of Zn, Cd, Ag and Ni may be used as catalysts. With a catalyst, the reaction may be conducted in a temperature range from about 125°–215° C., with the preferred range being 125°–150° C. The catalyst shows some effect at concentrations as low as 1%. However, it is preferred to use between 5 and 10 percent by weight of catalyst. At any point in the reaction, the degree of starting materials to product can readily be judged by gas chromatographic analysis. However, the reaction is reproducible and once convenient conditions, within the scope of this invention, have been established for conducting the reaction, the gas chromatographic analysis need not be conducted routinely.

The preferred method for conducting this decarboxylation is to use N-methyl-2-pyrrolidone as a solvent, 5 to 10% CuO as a catalyst, and to heat the solution for a period of 2–3 hours. Under these conditions the anhydride and the acid are fully converted to the desired product, and there seem to be no side products detectable by gas chromatography.

The difluorobenzoic acid may be isolated from the reaction mixture by acidifying the mixture and extracting with a suitable solvent such as ethyl acetate or diethyl ether. Evaporation of the solvent yields crude difluorobenzoic acid which may be recrystallized/decolorized by using water and activated carbon.

3,4-Difluorobenzoic acid may be nitrated in a mixture of nitric and sulfuric acids. The nitration is best conducted at a low temperature to avoid decarboxylation of the benzoic acid. In addition, it is a good idea to avoid an excess of nitric acid in conducting the nitration in order to avoid the formation of side products. The preferred procedure is to dissolve the 3,4-difluorobenzoic acid in sulfuric acid, and cool the solution on an ice bath. Nitric acid is then added slowly to the mixture. The mixture is then warmed to room temperature and stirred until the reaction is complete. The reaction mixture is then poured over ice, and the product, 2-nitro-4,5-difluorobenzoic acid, recovered.

2-nitro-4,5-difluorobenzoic acid may be reduced by many methods known to those skilled in the art. Two reduction methods are preferred in the practice of this invention. In the first, the 2-nitro-4,5-difluorobenzoic acid is mixed with iron powder and HCl, in solution, to form 4,5-difluoroanthranilic acid. The suitable solvents for conducting this reaction are water, mixtures of water and lower alcohols such as methanol, ethanol and propanol. Two to three moles of iron are used for each mole of the nitro compound. In the preferred procedure, the iron powder and 2-nitro-4,5-difluorobenzoic acid are mixed in a suitable solvent. The HCl is added and the solution is heated to a temperature between 60°–90° C. The mixture is stirred until the starting material disappears.

In the second preferred method of reduction, the 2-nitro-4,5-difluorobenzoic acid is treated with sodium formate in the presence of catalytic amounts of palladium on charcoal. The reaction is run either in aqueous solution, or in a mixture of water and a lower alcohol, such as methanol, ethanol, or propanol. An inorganic base such as sodium hydroxide, sodium carbonate, sodium bicarbonate, potassium hydroxide, potassium carbonate, potassium bicarbonate, or calcium hydroxide is added in sufficient quantities to create a pH of 7 to 8. The reduction is run at 60°–80° C., and the reaction mixture is stirred until the starting material is consumed. Reaction conditions must be selected carefully since the the fluorine para to the nitro group is rather labile, and can be removed if conditions become too forceful. For example, the equivalents of base should closely match the equivalents of the 2-nitro-4,5-difluorobenzoic acid being reduced because the flourine para to the nitro group may be displaced if the reaction mixture becomes too basic, leading to the formation of phenolic compounds.

The following specific examples are provided to further illustrate this invention and the manner in which it may be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

EXAMPLES

Example 1

Preparation of 3,4-difluorobenzoic acid 4,5-difluorophthalic anhydride (0.5 grams, 2.7 mmole) was added to a slurry of cupric oxide (5% by weight of starting material) in 5 ml. of N-methyl-2-pyrrolidone. n-tridecane (0.25 grams) was added as an internal standard. The mixture was heated to 190° C. for 3 hours, at which time GC analysis indicated complete consumption of the starting material and conversion to 3,4-difluorobenzoic acid in an 85% yield, based upon the internal standard, corrected for response factors.

Example 2

Preparation of 3,4-difluorobenzoic acid 4,5-difluorophthalic acid (0.55 grams, 2.7 mmole) was added to a slurry of cupric oxide (10% by weight of starting material) in 5 ml. of N-methyl-2-pyrrolidone solvent. n-tridecane (0.25 grams) was added as an internal standard. The mixture was heated to 190° C. for 3 hours, at which time GC analysis indicated complete consumption of the starting material and conversion to 3,4-difluorobenzoic acid in an 87% yield, based upon the internal standard, corrected for response factors.

Example 3

Preparation of 3,4-difluorobenzoic acid 4,5-difluorophthalic acid (0.55 grams, 2.7 mmole) was added to a slurry of cupric oxide (10% by weight) in dimethyl acetamide. The mixture was heated to 125° C. for 24 hours. Analysis by gas chromatography showed 70% 3,4-difluorobenzoic acid, 8% starting material and 25% other products.

Example 4

Preparation of 3,4-difluorobenzoic acid

Using a procedure similar to that of Example 3, 0.55 grams, (2.7 mmole) of 4,5-difluorophthalic acid was added to dimethyl acetamide. 10% $Cu_2O$ as a catalyst was added and the solution was heated at 125° C. for 24 hours. The yield of 3,4-difluorobenzoic acid was 70% (by gas chromatography).

Example 5

Preparation of 3,4-difluorobenzoic acid

Using a procedure similar to that of Example 3, 0.55 grams, (2.7 mmole) of 4,5-difluorophthalic acid was added to dimethyl acetamide. $Cu_2O$ as a catalyst was added and the solution was heated at 150° C. for 22 hours. The yield of 3,4-difluorobenzoic acid was 69% (by gas chromatography).

Example 6

Preparation of 3,4-difluorobenzoic acid

Using a procedure similar to that of Example 3, 0.5 grams, (2.7 mmole) of 4,5-difluorophthalic anhydride was added to N-methylpyrrolidone. 1% $Cu_2O$ as a catalyst was added and the solution was heated at 190° C. for 30 hours. The yield of 3,4-difluorobenzoic acid was 82% (by gas chromatography).

Example 7

Preparation of 3,4-difluorobenzoic acid

Using a procedure similar to that of Example 3, 0.5 grams, (2.7 mmole) of 4,5-difluorophthalic anhydride was added to N-methylpyrrolidone and the solution was heated at 190° C. for 30 hours. The yield of 3,4-difluorobenzoic acid was 79% (by gas chromatography).

Example 8

Nitration of 3,4-difluorobenzoic acid

Into 100 ml of 96% sulfuric acid was placed 3,4-difluorobenzoic acid (11.95 g, 0.0756 mol). The solution was stirred at room temperature until the DFBA was dissolved, and then cooled to 0° C. Nitric acid (7.9 g of 90% fuming) was added dropwise to the cooled mixture. After addition, the solution was warmed to room temperature and stirred until completion of the reaction. After pouring on to 500 g of ice water, the solids were filtered and washed with water. After drying, 11.88 g of 2-nitro-4,5-difluorobenzoic acid was isolated. The material was identified by GCMS and $^{19}$F NMR analysis. An additional 2.41 g of product was obtained by extraction of the acid washes and removal of the solvent.

Example 9

Reduction of 2-nitro-4,5-difluorobenzoic acid 2-nitro-4,5-difluorobenzoic acid (1.0 g, 0.0049 mol) was added to iron powder (0.83 g, 0.0148 mol) in 10 ml of 50% ethanol. 1 mL of concentrated HCl was added and the solution was heated to 80° C. After one hour, the starting material was completely gone and GC analysis indicated formation of 4,5-difluoroanthranilic acid by comparison with a known sample.

Example 10

Reduction of 2-nitro-4,5-difluorobenzoic acid 2-nitro-4,5-difluorobenzoic acid (1.0 g) was added to 10 mL of water. 0.2 g of NaOH was added, followed by 1.0 g of sodium formate. 0.05 g of 10% palladium on carbon was added, and the mixture was heated to 90° C. for 2.5 h. After cooling, a suitable internal standard was added. $^{19}$F NMR internal standard analysis of the entire reaction mixture indicated a 93% yield of 4,5-difluoroanthranilic acid.

We claim:

1. A process for the preparation of 4,5-difluoroanthranilic acid which comprises dissolving a starting material selected from the group consisting of 4,5-difluorophthalic anhydride and 4,5-difluorophthalic acid in a solvent selected from the group consisting of dimethyl acetamide, N-methyl-2-pyrrolidone and quinoline to form a solution, and heating said solution at a temperature between 175 and 215° C. to form 3,4-difluorobenzoic acid, nitrating said 3,4-difluorobenzoic acid in a mixture of nitric and sulfuric acids to form 2-nitro-4,5-difluorobenzoic acid, and reducing said 2-nitro-4,5-difluorobenzoic acid to form 4,5-difluoroanthranilic acid.

2. A process according to claim 1 wherein said 2-nitro-4,5-difluorobenzoic acid is reduced by reaction with a mixture of iron and HCl.

3. A process according to claim 1 wherein said 2-nitro-4,5-difluorobenzoic acid is reduced by reaction with sodium formate in the presence of a catalytically effective amount of a palladium on charcoal catalyst.

4. A process for the preparation of 4,5-difluoroanthranilic acid which comprises dissolving 4,5-difluorophthalic anhydride in a solvent selected from the group consisting of dimethyl acetamide, N-methyl-2-pyrrolidone and quinoline to form a solution, adding to the solution a catalytic amount of a catalyst selected from the group consisting of Cu, $Cu_2O$, CuO, copper salts, and oxides and salts of Zn, Cd, Ag and Ni and heating said solution at a temperature between 120 and 215° C. to form 3,4-difluorobenzoic acid, nitrating said 3,4-difluorobenzoic acid in a mixture of nitric and sulfuric acids to form 2-nitro-4,5-difluorobenzoic acid, and reducing said 2-nitro-4,5-difluorobenzoic acid to form 4,5-difluoroanthranilic acid.

5. A process according to claim 4 wherein said 2-nitro-4,5-difluorobenzoic acid is reduced by reaction with a mixture of iron and HCl.

6. A process according to claim 4 wherein said 2-nitro-4,5-difluorobenzoic acid is reduced by reaction with sodium formate in the presence of a catalytically effective amount of a palladium on charcoal catalyst.

7. A process according to claim 4 wherein said catalyst is metallic copper.

8. A process according to claim 7 wherein said 2-nitro-4,5-difluorobenzoic acid is reduced by reaction with a mixture of iron and HCl.

9. A process according to claim 7 wherein said 2-nitro-4,5-difluorobenzoic acid is reduced by reaction with sodium formate in the presence of a catalytically effective amount of a palladium on charcoal catalyst.

10. A process according to claim 4 wherein the catalyst is $Cu_2O$.

11. A process according to claim 10 wherein said 2-nitro-4,5-difluorobenzoic acid is reduced by reaction with a mixture of iron and HCl.

12. A process according to claim 10 wherein said 2-nitro-4,5-difluorobenzoic acid is reduced by reaction with sodium formate in the presence of a catalytically effective amount of a palladium on charcoal catalyst.

13. A process according to claim 4 wherein the catalyst is CuO.

14. A process according to claim 13 wherein said 2-nitro-4,5-difluorobenzoic acid is reduced by reaction with a mixture of iron and HCl.

15. A process according to claim 13 wherein said 2-nitro-4,5-difluorobenzoic acid is reduced by reaction with sodium formate in the presence of a catalytically effective amount of a palladium on charcoal catalyst.

16. A process for the preparation of 4,5-difluoroanthranilic acid which comprises heating dissolving 4,5-difluorophthalic acid in a solvent selected from the group consisting of dimethyl acetamide, N-methyl-2-pyrrolidone and quinoline to form a solution, adding to the solution a catalytic amount of a catalyst selected from the group consisting of Cu, $Cu_2O$, and CuO, copper salts, and oxides and salts of Zn, Cd, Ag and Ni and heating said solution at a temperature between 120° C. to 215° C. to form 3,4; -difluorobenzoic acid, nitrating said 3,4-difluorobenzoic acid in a mixture of nitric and sulfuric acids to form 2-nitro-4,5-difluorobenzoic acid, and reducing said 2-nitro-4,5-difluorobenzoic acid to form 4,5-difluoroanthranilic acid.

17. A process according to claim 16 wherein said 2-nitro-4,5-difluorobenzoic acid is reduced by reaction with sodium formate in the presence of a catalytically effective amount of a palladium on charcoal catalyst.

18. A process according to claim 16 wherein said 2-nitro-4,5-difluorobenzoic acid is reduced by reaction with a mixture of iron and HCl.

19. A process according to claim 16 wherein the catalyst is metallic copper.

20. A process according to claim 19 wherein said 2-nitro-4,5-difluorobenzoic acid is reduced by reaction with a mixture of iron and HCl.

21. A process according to claim 19 wherein said 2-nitro-4,5-difluorobenzoic acid is reduced by reaction with sodium formate in the presence of a catalytically effective amount of a palladium on charcoal catalyst.

22. A process according to claim 16 wherein the catalyst is $Cu_2O$.

23. A process according to claim 21 wherein said 2-nitro-4,5-difluorobenzoic acid is reduced by reaction with a mixture of iron and HCl.

24. A process according to claim 22 wherein said 2-nitro-4,5-difluorobenzoic acid is reduced by reaction with sodium formate in the presence of a catalytically effective amount of a palladium on charcoal catalyst.

25. A process according to claim 16 wherein the catalyst is CuO.

26. A process according to claim 29 wherein said 2-nitro-4,5-difluorobenzoic acid is reduced by reaction with a mixture of iron and HCl.

27. A process according to claim 25 wherein said 2-nitro-4,5-difluorobenzoic acid is reduced by reaction with sodium formate in the presence of a catalytically effective amount of a palladium on charcoal catalyst.

* * * * *